United States Patent [19]

Merz et al.

[11] 4,057,583

[45] Nov. 8, 1977

[54] PROCESS FOR THE PREPARATION OF PINACOLONE

[75] Inventors: Walter Merz, Leverkusen; Dieter Nachtsheim, Dormagen, both of Germany

[73] Assignee: Bayer Aktiengesellschaft, Leverkusen, Germany

[21] Appl. No.: 640,801

[22] Filed: Dec. 15, 1975

[30] Foreign Application Priority Data

Dec. 27, 1974 Germany .............................. 2461503

[51] Int. Cl.$^2$ ............................................. C07C 45/02
[52] U.S. Cl. ............................. 260/593 R; 260/597 R
[58] Field of Search ........................ 260/593 R, 597 R

[56] References Cited

FOREIGN PATENT DOCUMENTS

| 143,028 | 1/1962 | U.S.S.R. | ................................. 260/597 |
| 144,167 | 3/1962 | U.S.S.R. | ................................. 260/597 |

OTHER PUBLICATIONS

Nishimura et al., Chem. Abst., vol. 67, 73569K, (1967).
Hickihbottom, Reactions of Organic Compounds, pp. 33–34, (1957).
Nishimura et al., Chem. Abst., vol. 66, 37075S, (1960).

*Primary Examiner*—James O. Thomas, Jr.
*Assistant Examiner*—James H. Reamer
*Attorney, Agent, or Firm*—Burgess, Dinklage & Sprung

[57] ABSTRACT

The invention provides a novel synthesis for pinacolone comprising reacting 2-methyl-but-2-ene and/or 2-methyl-but-1-ene with an aqueous inorganic acid, adding formaldehyde gradually at a temperature between 50° and 200° C at a rate of 0.5 – 1.5 moles of formaldehyde per mole of butene compound, allowing the mixture to react further, and separating the pinacolone by distillation.

16 Claims, No Drawings

PROCESS FOR THE PREPARATION OF PINACOLONE

The present invention relates to a process for the preparation of pinacolone. This compound is useful as a solvent and as a starting material for further syntheses, for example for the preparation of known herbicidally active substances.

It has already long been known that pinacolone (2,2-dimethyl-3-oxo-butane) can be prepared from pinacol (2,3-dimethylbutane-2,3-diol) by treatment with dilute sulfuric acid (the "pinacol-pinacolone rearrangement"; see, for example, Beilsteins Handbuchder Organischen Chemie (Handbook of Organic Chemistry), 4th edition, volume I, page 694). However, this process has the great disadvantage that it is difficult to carry out on a large scale.

In order to obtain pinacol, acetone (I) is reduced with aluminum filings, mercury (II) chloride being added as an activator (see Beilstein, Supplementary Volume I, page 252):

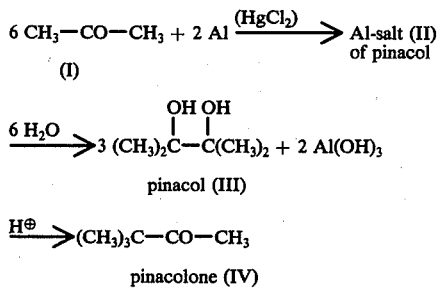

The particular disadvantage of this preparative method is that aluminum, which is expensive, is required as a starting material and that, based on aluminum, only yields of pinacolone which do not exceed 50–60% of theory are obtained. Since acetone is employed in a large excess and can be recovered in the pure form only with difficulty, the yield is even poorer when it is based on the consumption of acetone.

A further disadvantage of this process is that toxic mercury (II) chloride is required as the activator and the major part of this is converted into elementary mercury during the reaction. Despite working in a careful manner it is never possible quantitatively to isolate the mercury employed, so that considerable amounts of mercury pass into the effluent and into the outgoing air.

The fact that at the same time considerable amounts of aluminum salts are obtained, the separation of which as an aqueous solution or as solid aluminum hydroxide is associated with great difficulties and usually with loss of material, is to be regarded as a further disadvantage of this process. Even after they have been separated off, the aluminum salts cause problems because they cannot be further used and pass either into the effluent or to a dump.

The reaction is very highly exothermic and extremely vigorous and this is to be regarded as a further disadvantage of the known process. The reaction therefore requires special precautions, especially because it can be carried out only with absolutely dry starting materials. If the starting material is moist, the reaction either does not start at all or starts delayed, in an uncontrollable manner.

Moreover, a disadvantage of the synthesis of pinacolone via pinacol, which has been prepared by reduction of acetone, is that a total of three reaction stages are required:

1. Reduction of acetone with aluminum,
2. Hydrolysis of the aluminum salt of pinacol with water, and
3. Rearrangement of pinacol to give pinacolone.

It is also known that pinacolone is obtained when 4,4,5-trimethyl-1,3-dioxane (VI) is treated at the boil with acids, preferably dilute inorganic acids and also strong organic acids (see German Patent Specification No. 714,488). 4,4,5-Trimethyl-1,3-dioxane can be prepared easily in an approximately 80% yield by reacting aqueous formaldehyde with 2-methyl-but-2-ene (V) in the presence of acids (see Houben-Weyl-Müller, Methoden der Organischen Chemie (Methods of Organic Chemistry), Volume 6/3, page 266 et seq.):

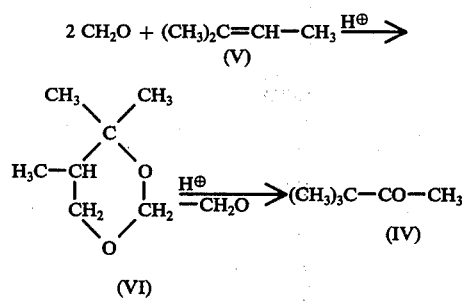

However, this process also has a number of disadvantages. Thus, in this case also more than one reaction step is required in order to obtain pinacolone from the starting materials which are available industrially.

Furthermore, according to the data given in German Patent Specification No. 714,488, it is not possible to force a reasonably complete conversion of 4,4,5-trimethyl-1,3-dioxane (VI) to pinacolone. In Example 1 of this patent specification the conversion is, for example, only 76.7%. Thus, the pinacolone formed is always contaminated with relatively large amounts of starting material, which has to be separated off by an additional process step. This is also necessary because, for economic reasons, the valuable starting material has to be re-used, after it has been separated off, for the preparation of pinacolone.

A further disadvantage is that a total of 2 moles of formaldehyde is required in order to prepare 1 mole of 4,4,5-trimethyl-1,3-dioxane (VI); 1 mole of this formaldehyde is liberated again during the subsequent splitting with acid and is thus lost and finally passes into the effluent, which thus has a very high oxygen demand for chemical or biological degradation.

However, a particular disadvantage of this method of preparation is the fact that only low yields are achieved. Thus, the maximum yield according to Example 1 of the patent specification mentioned is only 43.3% of theory, based on 4,4,5-trimethyl-1,3-dioxane employed, or 56.5% of theory, based on the conversion. This results, inter alia, in a considerable amount of by-products being obtained in the form of a viscous oil, which, when the reaction is carried out on an industrial scale, can be disposed of only by combustion.

The present invention provides a process for the preparation of pinacolone, which has the formula

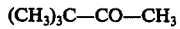

in which (1) a butene derivative selected from 2-methyl-but-2-ene, of the formula

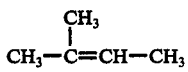
(V), 2-methyl-but-1-ene, of the formula

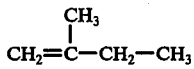
(VII), the addition products of the two said butenes, of the general formula

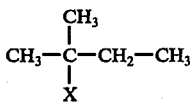
(VIII)

in which

X is Cl, Br, HSO$_4$ or H$_2$PO$_4'$ and mixtures of any of the compounds (V), (VII) and (VIII), is mixed with an aqueous solution of an inorganic acid, the aqueous phase of the mixture containing at least 15 percent by weight of acid and, while mixing (in general, intensively), optionally with the addition of a small amount of an emulsifier and optionally in the presence of a diluent, (2) formaldehyde, preferably in the form of an aqueous solution thereof or as paraformaldehyde, is added thereto over the course of 0.5 to 10 hours, at a pressure between 1 and 20 bars absolute and at a temperature of between 50° and 200° C, 0.5-1.5 moles of formaldehyde being added per mole of the butene derivative, the mixture being allowed to react for a further 0.5 to 3 hours, and the pinacolone is separated off by distillation, optionally after neutralization of the inorganic acid.

It is to be regarded as extremely surprising that, according to the reaction of the invention, pinacolone can be prepared in a single process step, the amount of formaldehyde required being only half that required by the prior art; considerably higher yields are nevertheless achieved. According to the process of the invention, yields of up to 75% of theory and above can be achieved. According to the state of the art, yields of at most 45.2% of theory (based on the 2-methyl-butene (V) or (VII) or addition product (VIII) employed) should be expected for yields of 4,4,5-trimethyl-1,3-dioxane (VI) of 80% of theory and yields of pinacolone of at most 56.5% of theory (based on the conversion of pure 4,4,5-trimethyl-1,3-dioxane). However since only half the amount of formaldehyde is used in the reaction according to the invention, a further fall in the yield would have to be expected according to the state of the art when the preparation of pinacolone from 2-methyl-but-2-ene is carried out in a single process step.

It is to be regarded as particularly surprising that it is also possible, with the aid of the process according to the invention, to obtain pinacolone from 2-methyl-but-1-ene (VII) in a one-stage reaction because this could not be expected with regard to the state of the art. As is known, 4-ethyl-4-methyl-1,3-dioxane of the formual (IX) is formed from 2-methylbut-1-ene (VII) and formaldehyde in the presence of acids (Prins reaction; see Houben-Weyl-Müller, Volume 6/3, page 265 et seq.):

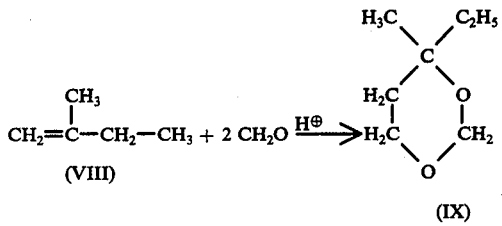

Conversion of the 1,3-dioxane derivative (IX) into pinacolone is not possible according to the state of the art.

Furthermore, it is to be regarded as surprising that it is also possible, with the aid of the reaction according to the invention, to convert the addition products of the general formula (VIII) into pinacolone. According to the state of the art it was not to be expected that the addition products (VIII), which are relatively stable under the reaction conditions, would enter into a reaction at all.

The process according to the invention has a number of advantages. Thus, it avoids all the disadvantages which are associated with the best process according to the state of the art, that is the reductive dimerization of acetone by means of aluminum to give pinacol and the subsequent rearrangement of this by means of sulfuric acid to give pinacolone.

Furthermore, the process according to the invention makes it possible for the first time to prepare the valuable intermediate product pinacolone in an economic manner from the raw materials 2-methyl-but-1-ene and 2-methyl-but-2-ene respectively and formaldehyde, since it is possible with the aid of the process according to the invention to carry out the reaction with high yields and at the same time to reduce the consumption of formalin to half and to obtain pinacolone in a one-stage process. In addition, the high yields reduce the amount of by-products and waste materials which are necessarily obtained and make the process less harmful to the environment than the processes of the prior art.

A particular technical advantage of the process according to the invention is that the mixtures obtained from the industrial preparation of 2-methyl-butene can be employed directly as starting materials.

If hydrochloric acid is employed as the inorganic acid, the course of the reaction can be represented by the set of formulae which follows:

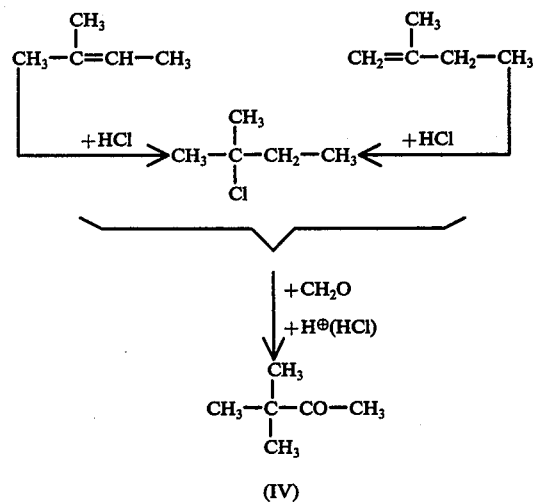

When 2-methyl-butene is prepared industrially, mixtures are obtained which normally contain 80–90% of 2-methyl-but-2-ene (V), 5–10% of 2-methyl-but-1-ene (VII) and other saturated or unsaturated hydrocarbons; these mixtures are suitable for use directly as starting materials for the process according to the invention.

The addition products of the formula (VIII), which can also be used as starting materials, and the preparation thereof are already known. Compounds which may be mentioned are: 2-chloro-2-methyl-butane, 2-bromo-2-methyl-butane, sulfuric acid 2-methyl-butyl monoester and phosphoric acid 2-methylbutyl monoester.

The formaldehyde required for the reaction according to the invention can be used in all the commercially available forms and concentrations; thus, it can, for example, be used as a 5–70% strength, preferably 20–60% strength, aqueous solution. However, paraformaldehyde can also be employed.

Possible diluents, in addition to water, are all inert solvents, especially hydrocarbons, such as pentane or hexane, and ketones, such as, for example, pinacolone. However, the use of solvents has no advantages for the reaction according to the invention, although it is unavoidable when the starting materials 2-methyl-but1-ene or 2-methyl-but-2-ene are not pure but also contain other hydrocarbons.

The reaction is generally carried out at temperatures between 50° and 200° C, preferably between 60° and 150° C.

The reaction can be carried out under normal pressure, but also under elevated pressure, this being the case when it is desired to reach temperatures which are above the azeotropic boiling point of the reaction mixture. In general, the reaction is carried out under pressures of between 1 bar and 20 bars absolute, preferably of from 1 bar to 10 bars absolute.

When carrying out the process according to the invention, 0.5–1.5 moles, preferably 0.8–1.1 moles of formaldehyde are generally employed per mole of 2-methyl-but-1-ene (VII) or of 2-methyl-but-2-ene (V) or of addition product (VIII). It is indeed possible to use less than 0.5 mole of formaldehyde but this results in no better yield, based on the conversion, and is uneconomical because of the low level of conversion associated therewith. Amounts of formaldehyde greater than 1.5 moles give no higher yield of pinacolone but merely impair the quality of the effluent.

Inorganic acids which can be used are, for example, hydrochloric acid, hydrobromic acid, sulfuric acid or phosphoric acid. The amount of inorganic acid required for the reaction according to the invention and the concentration of the acid in the aqueous solution depend on the nature of the acid. If hydrochloric acid or hydrobromic acid is used, the concentration thereof should be 20–40%. The amount of hydrochloric acid or hydrobromic acid must be so selected that the concentration of HCl or HBr in the aqueous phase of the reaction mixture is at least 15 percent by weight, preferably at least 18–20 percent by weight, this being the case during the entire reaction period (addition of formaldehyde and subsequent reaction), that is to say despite dilution due to aqueous formaldehyde being fed in, despite a fall in the concentration due to the loss of HCl gas or HBr gas into the atmosphere and despite a fall in the concentration due to the consumption of HCl or HBr in the formation of stable or unstable reaction products during the reaction, especially the formation of 2-chloro-2-methyl-butane or 2-bromo-2-methyl-butane.

If sulfuric acid or phosphoric acid is used, the concentration should be 20–60%. In this case also, the amount of acid must be so selected that the concentration of $H_2SO_4$ or $H_3PO_4$ is at least 15 percent by weight, preferably at least 20 percent by weight, during the entire reaction period.

It is essential for the reaction according to the invention that suitable measures are taken to ensure that the concentration of formaldehyde in the reaction mixture is kept low during the entire reaction period. This is preferably achieved by initially introducing 2-methyl-but-1-ene or 2-methyl-but-2-ene or an addition product of the formula (VIII) together with an aqueous solution of an inorganic acid and metering in the formaldehyde, preferably in the form of an aqueous solution or as a paraformaldehyde, at the rate at which it is consumed for the reaction according to the invention. The period over which the formaldehyde is run in should therefore be 0.5 to 10 hours, preferably 1–7 hours and the subsequent reaction time should be 0.5–3 hours.

It is also essential for the reaction according to the invention that provision is made for intensive mixing of the reaction mixture during the reaction and the subsequent reaction. This can be effected by using suitable stirrers and appropriate speeds of rotation of the stirrers but optionally also by adding small amounts of an emulsifier to the reaction mixture.

When the reaction is complete, and optionally after neutralization of the inorganic acid, pinacolone is distilled off azeotropically together with water from the reaction mixture, the distillation preferably being effected via a column in order to achieve a higher purity of the pinacolone. However, it is also possible to separate the two phases after the reaction is complete and to use all or part of the aqueous phase as aqueous inorganic acid for a renewed reaction. The organic phase which is separated off contains the pinacolone, which in this case also is isolated and purified most appropriately by distillation.

According to a particular embodiment, the reaction according to the invention can also be carried out continuously, preferably by using a reaction cascade and a distillation column which operates continuously.

Pinacolone can be used, for example, as an intermediate for the synthesis of known herbicidally active substances. In the following text the synthesis of 6-tert.-butyl-3-methylthio-4-amino-1,2,4-triazin-5(4H)-one (X), a compound having a herbicidal action, is described as an example (see U.S. Pat. No. 3,671,523).

1st Stage:

Pinacolone is converted according to a process known from the literature by oxidation with potassium permanganate into trimethylpyruvic acid [$(CH_3)_3$C-CO-COOH] (compare Monatshefte fur Chemie, Volume 10 (1889), page 771).

2nd Stage:

Analogously to instructions given by A. Dornow and others (Chem. Brichte 97 (1964), page 2173–2178), 53 g (0.5 mole) of thiocarbohydrazide are dissolved in 500 ml of boiling water and 65 g (0.5 mole) of trimethylpyruvic acid are added slowly. A colorless precipitate is deposited, which is filtered off, washed with water and dried in vacuo at 50° C. 6-tert.-butyl-3-mercapto-4-amino-1,2,4-triazin-5(4H)-one is obtained from this reaction in almost quantitative yield.

3rd Stage:

4 parts by weight of 6-tert.-butyl-3-mercapto-4-amino-1,2,4-triazin-5(4H)-one are dissolved in a mixture of 11 parts by weight of 2-normal sodium hydroxide and 4 parts by weight of methanol and the solution is treated at 0° C with 3.2 parts by weight of methyl iodide. The reaction mixture is then stirred for a further 4 hours at 20° C. The reaction product crystallizes out and is filtered off, dried and recrystallized from benzene. 3.52 parts by weight of 6-tert.-butyl-3-methylthio-4-amino-1,2,4-triazin-5(4H)-one of melting point 126°–127° C are obtained Yield: 82% of theory.

The process of this invention is illustrated by the following preparative examples.

EXAMPLE 1

1,665 g of 38% strength hydrochloric acid (630 g of 100% strength HCl) were initially introduced into a 4 liter flask with a brine-cooled reflux condenser, a thermometer, a stirrer and a dropping funnel. When 644 g (8.65 moles) of 2-methyl-butene (content: 86% of 2-methyl-but-2-ene and 8% of 2-methyl-but-1-ene) were run in, an exothermic reaction took place and the reaction temperature was kept below 50° C by cooling slightly. After the mixture had been further stirred for a short time, introduction of 865 g (8.65 moles) of 30% strength formalin was started at 50°–55° C and took place uniformly over 5–6 hours, the mixture being kept at boil and stirred intensively. While the formalin was running in, the boiling point rose continuously and finally reached about 88°–93° C. When introduction of formalin was complete, the mixture was allowed to react for a further 2 hours and, after neutralizing the mixture with sodium hydroxide solution, the pinacolone which had formed was distilled off azeotropically with water from the reaction mixture.

If a column is used for this distillation, the pinacolone can be obtained direct in high purity (>99%) after separating off the water which has also distilled over.

Yield: 650 g (75% of theory, based on the 2-methyl-but-2-ene and 2-methyl-but-1-ene employed).

EXAMPLE 2

In the same manner as has been described in Example 1, 644 g (8.65 moles) of 2-methyl-butene (content: 86% of 2-methyl-but-2-ene and 8% of 2-methyl-but-1-ene) were added to 3,200 g of 30% strength hydrochloric acid (960 g of 100% strength HCl) and the mixture was reacted with 865 g (8.65 moles) of 30% strength formalin. On working up, 653 g (75.5% of theory) of pinacolone were obtained.

EXAMPLE 3

In the same manner as has been described in Example 1, 482 g (6.45 moles) of 2-methyl-butene (contents: 86% of 2-methyl-but-2-ene and 8% of 2-methyl-but-1-ene) were added to 1,250 g of 38% strength hydrochloric acid (475 g of 100% strength HCl) and the mixture was reacted with 462 g (4.62 moles) of 30% strength formalin. On working up, 385 g (59.5% of theory) of pinacolone and 82 g (12% of theory) of 2-chloro-2-methylbutane were obtained (total yield thus 71.5% of theory).

EXAMPLE 4

In the manner described in Example 1, 482 g (6.45 moles) of 2-methyl-butene (content: 86% of 2-methyl-but-2-ene and 8% of 2-methyl-but-1-ene) were added to 1,250 g of 38% strength hydrochloric acid (475 g of HCl) and the mixture was reacted with 726 g (7.26 moles = 105% of theory) of 30% strength formalin. On working up, 442 g (68.5% of theory) of pinacolone, which was completely free from 2-chloro-2-methyl-butane, were obtained.

EXAMPLE 5

A mixture of 350 ml of concentrated hydrochloric acid (38% strength) and 80.5 g of 2-methylbutene (content 86% of 2-methyl-but-2-ene and 9% of 2-methyl-but-1-ene) was brought to the boil under a reflux condenser; a suspension of 30 g of paraformaldehyde in 70 ml of water was added dropwise in the course of 5 hours. On working up in the manner described in Example 1, a distillate was obtained which contained 53.4 g (49.5% of theory) of pinacolone and 13.0 g (11.3% of theory) of 2-chloro-2-methyl-butane. (Total yield: 60.8% of theory).

EXAMPLE 6

107 g of 38% strength hydrochloric acid were added to 53 g of 2-chloro-2-methyl-butane (0.46 mole) which had a boiling point of 82°–85°. 55 g of 30% strength formalin were added dropwise in the course of 5 hours to the boiling mixture, which was stirred, the reflux temperature rising from 42° C at the start to 92° C. The customary working up by distillation gave 27.2 g of pure pinacolone, that is to say 59.2% of theory.

EXAMPLE 7

At a maximum temperature of 30° C, 70 g (1.0 mole) of pure 2-methyl-but-1-ene were added dropwise to 210 g of 38% strength hydrochloric acid, whilst cooling. After heating the mixture to the reflux temperature, 110 g of 30% strength formalin (1.1 moles) were added dropwise in the course of 5 hours, the reflux temperature rising to 91° C. The customary working up gave 67 g of pure pinacolone (67% of theory).

EXAMPLE 8

According to the procedure described in Example 1, 644 g (8.65 moles) of 2-methyl-butene (content: 86% of 2-methyl-but-2-ene and 8% of 2-methyl-but-1-ene were reacted with 1,665 g of 38% strength hydrochloric acid and 880 g of 30% strength formalin solution. When the reaction was complete, the organic phase was separated off. The HCl content in the aqueous phase was 21 – 22% and was brought up to 38% by passing in hydrogen chloride. 1,665 g of this crude 38% strength hydrochloric acid, thus obtained, were used for renewed reaction of 2-methyl-butene with formaldehyde to give pinacolone. This procedure was carried out 4 times in succession. When the hydrochloric acid, which was reconcentrated again each time was used for the 4th time, 630 g of pinacolone (73.0% of theory) were obtained.

EXAMPLE 9

60 g (0.085 mole) of 2-methyl-butene (content: 86% of 2-methyl-but-2-ene and 8% of 2-methyl-but-1-ene) were added to 265 ml of 20% strength sulfuric acid in an Euzonit autoclave. The mixture was warmed to 110° C in the closed autoclave. In the course of 4 hours, 175 g of 15% strength formaldehyde solution were pumped in at this temperature whilst stirring intensively, the pressure rising to a maximum of 7 bars absolute. After stirring for a further hour at 110° C, the pH was adjusted to 8 with 60 ml of 50% strength sodium hydroxide solution. Pinacolone was isolated in the customary manner by steam distillation through a packed column. The distillate contained 37.1 g of pinacolone, that is to say 46.1% of theory.

EXAMPLE 10

60 g (0.805 mole) of 2-methyl-butene (content: 86% of 2-methyl-but-2-ene and 8% of 2-methyl-but-1-ene) were added to 265 ml of 30% strength sulfuric acid in an Euzonit autoclave. The mixture was warmed to 100° C in the closed autoclave. In the course of 2 hours, 82.5 g of 30% strength formalin were pumped in at this temperature. During this addition, the reaction mixture was stirred intensively and the pressure rose to a maximum of 5.1 bars absolute. After neutralization and customary working up, a distillate was obtained which contained 36.2 g of pinacolone, that is to say 45.0% of theory.

EXAMPLE 11 (continuous process)

a. There is provided a jacketed vessel, with a stirrer, a side outlet at about its middle, an outlet condenser, a jacketed dropping funnel, a reflux condenser and a gas inlet pipe communicating with the space at the top of the vessel. The yield is about 96% of theory. 400 ml of isoamylene (approximately 85% of methylbutene-2, 5% of methyl-butene-1, 10% pentanes) and 900 ml of 30% hydrochloric acid are first introduced into the reaction vessel. While stirring, the mixture is heated and brought to the boil at a temperature of about 70°-72° C. Thereafter 15 liters per hour of HCl gas are introduced into the gas space and isoamylene simultaneously added dropwise at such a rate that the temperature in the liquid is kept between 65° and 70° C under reflux conditions. The upper organic layer is continuously withdrawn via a condenser from the side delivery pipe in an amount corresponding to the amount of isoamylene added. Any hydrochloric acid carried along with the organic layer is separated off and recycled to the vessel. The organic layer thus removed consists of tertiary amyl chloride in an amount of approximately 95% and can be directly employed for further reaction.

b. If there is no readily available source of HCl gas, the process of (a) can be repeated except 30% hydrochloric acid is dropped into the vessel instead of HCl gas at the rate required to maintain the 65°-70° C temperature. The side stream comprises organic material and hydrochloric acid at about 22% concentration, the two being separated after condensation.

c. A vessel as in (a) is charged with 770 ml of 22% hydrochloric acid. The hydrochloric acid is heated while stirring to 85° C and amyl chloride and formalin are added dropwise in a ratio of 1:1 at a reflux temperature of 75° C to 80° C. A mixture of crude pinacolone and hydrochloric acid of approximately 20% concentration is removed from the side outlet and treated with concentrated sodium hydroxide solution. The crude pinacolone is then separated off as the top layer from the alkaline salt water. From 900 g of amyl chloride of 95,3% purity (corresponding to 857.5 of 100% amyl chloride, corresponding to 805g of pinacolone) there are obtained 1080 ml of crude pinacolone of approximately 86% purity. 562g of pure pinacolone are obtained by means of distillation, corresponding to at least 70% of theory. The content of amyl chloride in the crude pinacolone can be reduced to a value below 0.5% by increasing the amount of formalin, or alternatively the first runnings of the pinacolone distillation can be recycled into the amyl chloride reaction. In addition, 2370 ml of alkaline waste water (effluent) are obtained.

The amount of effluent is influenced by the concentration of formaldehyde solution and by the use of hydrogen chloride gas or hydrochloric acid. Formalin is normally employed with a 30% content of formaldehyde but a formaldehyde solution of higher concentration can also be employed.

It will be understood that the specification and examples are illustrative but not limitative of the present invention and that other embodiments within the spirit and scope of the invention will suggest themselves to those skilled in the art.

What is claimed is:

1. Process for the preparation of pinacolone which process comprises
  1. mixing a butene compound selected from
    a. 2-methyl-but-2-ene of the formula

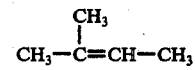

b. 2-methyl-but-1-ene of the formula

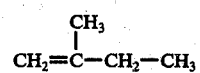

c. the addition products of the two said butenes of the general formula

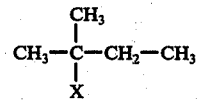

in which
      X is Cl, Br, HSO$_4$ or H$_2$PO$_4$,
    and mixtures of said compounds with an aqueous solution of hydrochloric or hydrobromic acid to provide 15% to 40% by weight of said acid in the aqueous phase of the resulting mixture;
  2. adding formaldehyde to the resulting mixture over a period of 0.5 to 10 hours, at a pressure of from 1 to 20 bars (absolute) and at a temperature of from 50° to 200° C. at a rate of 0.5 to 1.5 moles of formaldehyde per mole of butene compound,
  3. allowing the mixture to react for an additional period of 0.5 to 3 hours; and
  4. separating off the pinacolone by distillation.

2. Process as claimed in claim 1 comprising the addition of an emulsifier to the mixture of step (1) prior to adding the formaldehyde in step (2).

3. Process as claimed in claim 1 wherein said acid is neutralized prior to the separation of pinacolone in step (4).

4. Process as claimed in claim 1 wherein the formaldehyde employed in step (2) is supplied in the form of an aqueous solution thereof.

5. Process as claimed in claim 1 wherein the formaldehyde employed in step (2) is supplied in the form of paraformaldehyde.

6. Process as claimed in claim 4 wherein the said aqueous solution of formaldehyde is of a concentration of 5 to 70% by weight.

7. Process as claimed in claim 1 wherein the reaction of step (3) is carried out at a temperature of from 60° to 150° C.

8. Process as claimed in claim 1 wherein the reaction of step (3) is carried out at a pressure of from 1 to 10 bars (absolute).

9. Process as claimed in claim 1 wherein at least 0.8 moles of formaldehyde are used per mole of said butene compound.

10. Process as claimed in claim 1 wherein said butene compound is a mixture of 2-methyl-but-1-ene and 2-methyl-but-2-ene.

11. Process as claimed in claim 1 wherein said acid is in an aqueous solution of a concentration of 20 to 40% by weight of acid.

12. Process as claimed in claim 1 wherein the formaldehyde added in step (2) is added over a period of 1 to 7 hours.

13. Process as claimed in claim 1 wherein the reaction is carried out continuously.

14. Process as claimed in claim 13 wherein the reaction is carried out continuously by using a reaction cascade and a distillation column which operates continuously.

15. Process as claimed in claim 1 wherein said butene compound is 2-methyl-but-2-ene.

16. Process as claimed in claim 1 wherein said butene compound is 2-methyl-but-1-ene.

* * * * *